United States Patent
Karabulut

(10) Patent No.: US 12,372,514 B2
(45) Date of Patent: Jul. 29, 2025

(54) METHOD FOR USE IN DETERMINATION OF APOPTOTIC SPERMS

(71) Applicant: ISTANBUL MEDIPOL UNIVERSITESI, Istanbul (TR)

(72) Inventor: Seda Karabulut, Istanbul (TR)

( * ) Notice: Subject to any disclaimer, the term of this patent is extended or adjusted under 35 U.S.C. 154(b) by 1049 days.

(21) Appl. No.: 17/264,381

(22) PCT Filed: Aug. 9, 2019

(86) PCT No.: PCT/TR2019/050677
§ 371 (c)(1),
(2) Date: Jan. 29, 2021

(87) PCT Pub. No.: WO2020/032906
PCT Pub. Date: Feb. 13, 2020

(65) Prior Publication Data
US 2021/0270811 A1    Sep. 2, 2021

(30) Foreign Application Priority Data
Aug. 10, 2018 (TR) .................. 2018/11634

(51) Int. Cl.
*G01N 33/50* (2006.01)
*G01N 33/545* (2006.01)

(52) U.S. Cl.
CPC ....... *G01N 33/5044* (2013.01); *G01N 33/545* (2013.01)

(58) Field of Classification Search
None
See application file for complete search history.

(56) References Cited

U.S. PATENT DOCUMENTS

| 6,245,808 B1 * | 6/2001 | Uckun | A61P 35/00 |
| | | | 514/492 |
| 2012/0270204 A1 * | 10/2012 | Fox | C12N 5/0612 |
| | | | 977/773 |
| 2017/0045500 A1 | 2/2017 | Cohen | |

FOREIGN PATENT DOCUMENTS

| AU | 2016247202 B2 | 8/2018 | |
| WO | WO-2014090802 A1 * | 6/2014 | ........... C12N 5/0612 |

OTHER PUBLICATIONS

Said "Effects of advanced selection methods on sperm quality and Art outcome: a systematic review" Human Reproduction Update 2011 17:719 (Year: 2011).*
Karabulut et al. Theriogeneology 2022 194:92-103 (Year: 2022).*
2022.*
2011.*
WO2014090802 Machine English Translation (Year: 2014).*
International Search Report for corresponding PCT/TR2019/050677, dated Jan. 24, 2020.
Written Opinion of the International Searching Authority for corresponding PCT/TR2019/050677, dated Jan. 24, 2020.

* cited by examiner

*Primary Examiner* — Changhwa J Cheu
(74) *Attorney, Agent, or Firm* — Egbert, McDaniel & Swartz, PLLC

(57) ABSTRACT

Disclosed is a method for live detection of apoptotic sperms contained in a sperm sample under in vitro conditions.

5 Claims, No Drawings

METHOD FOR USE IN DETERMINATION OF APOPTOTIC SPERMS

TECHNICAL FIELD

The present invention relates to a method for live detection of apoptotic sperms contained in a sperm sample used in assisted reproduction techniques under in vitro conditions.

STATE OF THE ART

In microinjection method (ICSI—Intracytoplasmic sperm injection), which is the most important method used in the treatment of infertility also known as IVF, a sperm is placed into an oocyte with the help of micromanipulator.

The quality of sperm and oocyte are two factors that directly affect embryo development and success. Since the number of oocytes is limited (average 10), it is not possible to select the oocyte, thus all oocytes are used for microinjection, while the high number of sperm (on average 10 million) makes it possible to select sperms. However, only morphological criteria are used in the selection of sperm, which does not reflect the genetic, metabolic and functional status of the sperm.

As in all cells, the mechanism of apoptosis in sperm is an elimination mechanism triggered by a problem in the internal dynamics of the cell. By triggering this mechanism known as programmed cell death, the cell destroys itself. Apoptosis is a mechanism that indirectly demonstrates these internal problems, as it activates the internal control mechanism of unhealthy sperm for any reason (genetic, metabolic or functional).

The use of non-apoptotic sperms in the selection of healthy sperm will make it possible to select a healthy sperm.

DNA fragmentation and activations of Caspase enzymes, which are the most important indicators of apoptosis, are generally used for the determination of apoptosis in sperm, but all these techniques can only be applied to fixated or lysed dead sperm. Apoptosis rates determined in sperms as a result of the application of these techniques are given as a percentage for a particular patient and are used only to inform the patient.

The cut-off value of the DNA fragmentation rate is generally accepted as 30%. It is known that fertilization rates, embryo development, embryo quality, implantation, pregnancy and live birth rates decrease and abortion rates are increased in individuals with apoptosis levels above this rate. This is of great importance in a IVF cycle where the chances of success cannot exceed 40% even in couples with the best cohort, because the patient's failure to conceive requires a new cycle to be tried, which leads to a loss of money and time and increases the likelihood of medical complications, not to mention that it is psychologically and socially challenging for the couple. The high chance of success in people with low or no apoptosis is also proof of this situation. However, it is known that approximately half of the patients receiving infertility treatment are male, and the rate of apoptosis is higher in these patients. It has been shown that this rate increases in the infertility group with unknown cause, which is called unexplained infertility, and that this may be the cause of the problem in the majority of patients in this group.

In the light of all this information, it is very important that healthy sperm can be selected alive.

In the state of the art, separation of apoptotic and non-apoptotic sperm can be performed using flow-cytometry. However, given that this method is very expensive in both fixtures used and consumables, and that the method is applied in very few center and, require extra training and experience and that the process is not sterile leads to use of this method only for research purposes.

In view of the present situation, there appears to be a need for a cost-effective, easily applicable method that can be used to isolate apoptotic sperms contained in a sperm sample by marking them live.

For this purpose, unlike the known techniques, instead of a sperm selection method based solely on motility and morphology, it is aimed to develop a method which provides indirect information about the metabolic, genetic and functional status of sperm.

DETAILED DESCRIPTION OF THE INVENTION

The present invention is directed to the use of a light microscopic technique that allows for the in vitro labeling of apoptotic sperm from a sperm sample, thereby allowing the identification of non-apoptosis-detected sperm.

The method according to the invention is distinguished from the methods known in the art because it allows the analysis of live sperms, allows the selection of non-apoptotic sperms for microinjection (ICSI) method, allows to work under sterile conditions, and that it dose not require use of an extra equipment and training.

In one aspect, the invention relates to a method for the detection of apoptotic sperms in an in vitro sperm sample, wherein said method comprises the steps of;
  a. Preparation of latex beads coated with a protein having phosphatidylserine affinity
  b. Treatment of prepared latex bead with prepared sperm sample
  c. Evaluation of sperm sample using light microscope
  d. Identification of sperms that are attached to latex beads as apoptotic sperms.
  e. Optionally, selecting the healthy sperms that did not adhere to the the latex bead and using them.

In a preferred embodiment of the invention, step a) comprises the steps of; a1) pre-treating the latex beads; and a2) coating the pre-treated latex beads with a protein having affinity for phosphatidylserine.

In a preferred embodiment of the invention, step a1) comprises the steps of diluting the latex bead solution, preferably a solution of 40 mg/ml IDC UltraClean Amidine latex bead solution, in a suitable buffer, preferably with 0.025M, pH 6 MES buffer (2-(N-morpholino) ethanesulfonic acid), discarding the supernatant then re-diluting the remaining particles with buffer, preferably with 0.025M, pH 6 MES buffer (2-(N-morpholino) ethanesulfonic acid), centrifugation of the particles and discarding the supernatant and then suspending the remaining particles with a suitable buffer, preferably with 0.025M, pH 6 MES buffer (2-(N-morpholino) ethanesulfonic acid), so as to form a 2% solution.

In a preferred embodiment of the invention, step a2) comprises the steps of addition of 50 mg/ml of EDAC (1-Ethyl-3-(3-dimethylaminopropyl carbodiimide) solution in a suitable buffer, preferably 0.025M, pH 6 MES (2-(N-morpholino)ethane sulfonic acid) buffer (e.g. 100 mg EDAC in 2 ml MES), to the latex bead solution obtained in step a1), addition of a protein that has phosphatidylserine affinity in a suitable buffer, preferably in 0.025M, pH 6 MES (2-(N- morpholino)ethane sulfonic acid), to said solution, incubating the mixture at room temperature for 2-5 hours, then centrifuging the mixture to remove free protein from the latex beads that bind to the protein that has phosphatidylserine affinity, after discarding the supernatant, the particles are diluted with PBS ((phosphate buffered saline solution/buffer) 0.1M, pH 7.2) followed by centrifuge, optionally repeating this process 3-4 times, after discarding the supernatant suspending the precipitate (pellets) in the storage buffer (0.1 M PBS, 0.1% glycine, 0.1% sodium azide, pH 7.2) at a concentration of 1%.

As used herein, the term "protein with phosphatidylserine affinity" refers to proteins with a double-layered lipid structure and susceptible to binding to phosphatidylserine on the outer surface of apoptotic cells. Proteins with phosphatidylserine affinity are selected from a group comprising annexins, protein kinase C (PKC), synaptotagmin, phospholipase C (PLC), rabfilin, DOC1, DOC2, MARCKS, Vinculin, Lactadherin, Gas-6, Raf-1, DGK, SK1, NO synthase, FGF.

Annexins mentioned herein are selected from a group comprising Annexin type I, Annexin type II, Annexin type III, Annexin type IV, Annexin type V (or Annexin A5), Annexin type VI, Annexin giardin, Annexin type VII, Annexin type VIII, Annexin type X, Annexin type XI, Annexin type XIII, Annexin type XIV, Annexin type XXXI In a preferred embodiment of the invention, Annexin that have phosphaditylserine affinity is particularly preferably Annexin V (Annexin A5).

In one embodiment of the invention, proteins with affinity for phosphatidylserine may be used in conjugation with a fluorescent or an enzymatic tag or biotin.

During the application of the process according to the invention, solutions that would help realizing the process can be for example prepared with water or any other suitable buffer solution that are readily accessible to the person skilled in the art.

Another aspect of the invention is the use of a method according to the invention for determining the amount of apoptotic sperms in a sperm sample.

Another aspect of the invention is the use of the method according to the invention for separating healthy sperm from apoptotic sperm in a sperm sample.

In a preferred embodiment of the invention, the sperm determined to be apoptotic sperm by the method according to the invention can be selected and separated from healthy sperm under microscope.

The invention will now be described by way of example only with reference to the following examples, which are intended to be exemplary only and are not to be construed in any way as limiting the scope of the invention.

EXAMPLES

Example 1: Production of Annexin V Coated Latex Beads a) Pre-Treatment of Latex Beads First, 2.5 ml (40 mg/ml) of the IDC UltraClean Amidine Latex bead solution is diluted in 10 ml 0.025M, pH 6 MES buffer (2-(N-morpholino) ethanesulfonic acid). The mixture is then centrifuged to precipitate the particles. The supernatant is discarded and 10 ml of MES buffer is added again to the mixture, centrifuged again and the supernatant is separated from the particles and discarded. 5 ml MES buffer was added to the obtained latex beads to suspend the beads to obtain Latex beads ready for Annexin V coating (as a 2% solution).

B) Coating of Pre-Treated Latex Beads with a Protein Having Affinity for Phosphatidylserine To the prepared 2% latex bead solution, a solution of EDAC (1-Ethyl-3-(3-dimethylaminopropyl carbodiimide) with 50 mg/ml in MES buffer (eg 100 mg EDAC in 2 ml MES) is added. Annexin V antibody is then added to the solution in 5 ml MES buffer (containing 5 mg antibody). The mixture is incubated at room temperature with shaking for 3-4 hours. The mixture is then centrifuged to separate the free Annexin V with latex beads attached to Annexin V. The supernatant is discarded. The precipitate (pellet) is suspended in 10 ml of PBS (phosphate buffered saline solution/buffer, 0.1M, pH 7.2). The particles are centrifuged again to precipitate. This washing step is repeated 3-4 more times using PBS. Finally, the pellet is suspended in 10 ml of storage buffer (0.1 M PBS, 0.1% glycine, 0.1% sodium azide, pH 7.2) and brought to a concentration of 1%.

Example 2: Detection of Apoptotic Sperm Cells Using Annexin V-Bound Latex Beads

Annexin V coated latex bead solution and the liquefied semen sample are mixed in vitro on a slide in a 1:1 ratio and kept for 1-5 minutes, preferably 2 minutes. The sperm are then evaluated under a light microscope, preferably using a 40× objective. Since the apoptotic sperm cells in the semen sample are bound to Annex in V, these sperm will appear to be surrounded by latex beads and will be classified as apoptotic sperm cells. Sperm cells not surrounded by latex beads will be classified as healthy sperm without apoptosis. In this way, healthy sperm not surrounded by beads can be selected for microinjection.

Around these basic concepts, it is possible to develop a wide variety of applications relating to the subject matter of the invention, the invention being not limited to the examples described herein, but essentially as set forth in the claims.

It is evident that a person skilled in the art can demonstrate the novelty disclosed in the invention using similar embodiments and/or may apply this embodiment to other fields of similar purpose as are used in the art. It is therefore evident that such embodiments will lack the criterion of innovation and in particular overcome the prior art.

The invention claimed is:

1. A method of in vitro detection of an apoptotic sperm in a sperm sample, the method comprising:
   coating a latex bead with a protein having phosphatidylserine affinity;
   treating the coated latex bead with the sperm sample without addition of labeling material;
   evaluating the treated sperm sample by using a light microscope; and
   identifying the apoptotic sperm attached to the coated latex bead by the light microscope.

2. The method of claim 1, wherein the step of identifying comprising:
   identifying sperms defined as apoptic in the sperm sample.

3. The method of claim 1 used for quantifying apoptic sperm in a sperm sample under in vitro conditions.

4. The method of claim 1, further comprising:
   separating healthy sperm from apoptic sperm in the sperm sample under in vitro conditions.

5. The method of claim 1, wherein the step of identifying comprises:
  detecting the apoptic sperm in the sperm sample under in vitro conditions.

* * * * *